United States Patent [19]

Chester et al.

[11] 4,350,835
[45] Sep. 21, 1982

[54] PROCESS FOR CONVERTING ETHANE TO AROMATICS OVER GALLIUM-ACTIVATED ZEOLITE

[75] Inventors: Arthur W. Chester; Yung F. Chu, both of Cherry Hill, N.J.

[73] Assignee: Mobil Oil Corporation, New York, N.Y.

[21] Appl. No.: 235,777

[22] Filed: Feb. 19, 1981

[51] Int. Cl.³ .................. C07C 12/02; C07C 12/42
[52] U.S. Cl. .................. 585/415; 585/417; 585/419; 252/455 Z
[58] Field of Search ..................... 585/415

[56] References Cited

U.S. PATENT DOCUMENTS

| | | | |
|---|---|---|---|
| 3,926,781 | 12/1975 | Gale | 585/415 X |
| 4,056,575 | 11/1977 | Gregory et al. | 585/415 X |
| 4,157,356 | 6/1979 | Bulford | 585/415 |
| 4,180,689 | 12/1979 | Davies et al. | 585/415 X |
| 4,238,318 | 12/1980 | Kouwenhoven | 585/415 X |

*Primary Examiner*—Paul F. Shaver
*Attorney, Agent, or Firm*—Charles A. Huggett; Michael G. Gilman; Van D. Harrison, Jr.

[57] ABSTRACT

A catalytic process is provided for converting gaseous feedstocks containing ethane to liquid aromatics by contacting said gaseous feeds in the absence of added air or oxygen, under conversion conditions, with a crystalline zeolite catalyst having incorporated therein a minor amount of gallium, thereby converting the ethane in the feedstock to aromatics and recovering a liquid mixture of benzene, toluene and xylene.

15 Claims, No Drawings

PROCESS FOR CONVERTING ETHANE TO AROMATICS OVER GALLIUM-ACTIVATED ZEOLITE

BACKGROUND OF THE INVENTION

1. Field of the Invention

This invention relates to a process for the conversion of a gaseous paraffinic feed containing ethane to liquid aromatics in the presence of a crystalline zeolite catalyst.

2. Description of the Prior Art

Zeolites and alumina have been used in the past in the preparation of catalysts for the production of aromatic hydrocarbons from open chain hydrocarbons. The open chain hydrocarbon is passed over the catalyst at an elevated temperature in the liquid or vapor phase. Zeolites of various types, particularly those containing a high silica-to-alumina ratio, have been suggested for the preparation of such catalysts. Examples of such zeolites are mordenite and the ZSM varieties. Such zeolites have been known to contain gallium in the form of its oxide which is substituted either partially or wholly for the aluminium oxide present therein. These zeolites however contain gallium as part of the crystal structure of the zeolite and the gallium is non-ionic. However, the yields of aromatic hydrocarbons from such open chain hydrocarbons have been unsatisfactory when using catalysts prepared from such zeolites.

U.S. Pat. No. 4,180,689 teaches that by using catalysts which contain gallium and which are prepared from specific types of aluminosilicates improved yields of aromatic hydrocarbons may be obtained if gallium-containing catalysts are prepared from specific types of aluminosilicates. This patent further discloses that if the gallium is either exchanged for one of the cations or protons or impregnated into the zeolite cavities surprisingly high catalytic activity is obtained especially in hydrocarbon conversion process. The feedstocks for this process are $C_3$–$C_{12}$ feedstock of either a single component or mixtures of saturated and unsaturated hydrocarbons.

U.S. Pat. No. 4,120,910 discloses that aromatic compounds can be produced by contacting, in the absence of added air or oxygen under suitable conversion conditions a gaseous, paraffinic feed stock containing a high percentage of ethane with a ZSM-5 type crystalline aluminosilicate zeolite catalyst having incorporated therein a minor amount of a metal or metal oxide from Group VIII, IIB, or IB. Especially preferred is a zinc-copper mixture.

SUMMARY OF THE INVENTION

Briefly stated, this invention comprises a process for producing aromatic compounds which comprises contacting, in the absence of added air or oxygen, under suitable conversion conditions a gaseous, paraffinic feed containing a high percentage of ethane with a ZSM-5 type crystalline aluminosilicate zeolite catalyst having gallium deposited thereon or in which cations have been exchanged with gallium ions, whereby ethane present in said gaseous feed is converted to aromatic compounds and recovering said aromatic compounds as liquids.

DESCRIPTION OF SPECIFIC EMBODIMENTS

Accordingly, the present invention is a process for producing aromatic hydrocarbons comprising bringing into contact at an elevated temperature a hydrocarbon feedstock and a catalyst composition comprising a zeolite having gallium deposited thereon and/or whose cations have been exchanged with gallium ions.

The gallium in the catalyst composition may be present as gallium oxide and/or as gallium ions if cations in the alumino silicate support have been exchanged with gallium ions. In the case where the cations in the zeolite have been exchanged for gallium ions, the gallium ion is suitably provided as an aqueous solution of gallium salts such as for instance gallium nitrate, gallium chloride or gallium sulphate. Such catalysts may be produced by conventional ion exchange techniques and the catalysts so produced are subsequently dried. For example, an aqueous solution of a gallium compound such as gallium nitrate may be placed in contact with the zeolite at ambient or elevated temperature, e.g. by refluxing. The exchanged zeolite is then separated by decantation followed by filtration, washed several times with deionised water and finally dried. Before addition to the aqueous solution of the gallium compound, the zeolite may be acid treated.

The process of the present invention may also be carried out using catalysts in which gallium is only impregnated on the surface of the zeolite or is incorporated in the intracrystalline zeolite cavities as a gallium compound which gives rise to gallium oxide during activation of the catalyst prior to contact with the hydrocarbon feedstock.

Where the catalyst composition is prepared by using a compound of gallium which ionises in aqueous solution for example gallium nitrate, it is inevitable that some of the gallium ions will be exchanged with the cations in the zeolite even if the preparation was directed to impregnation of the zeolite.

Whichever method of catalyst preparation is used, the amount of gallium present in the catalyst compositions (gallium plus zeolite) may vary for instance between 0.05 and 10%, preferably between 0.5 and 5% by weight.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also included within this definition are substantially pure silica analogs of the useful zeolites described herein, that is to say those zeolites having no measurable amount of aluminum (silica to alumina mole ratio of infinity) but which otherwise embody the characteristics disclosed.

This novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

$$(0-15)RN:(0-1.5)M_{2/n}O:(0.2)Al_2O_3:(100)SiO_2$$

wherein:

M is at least one cation having a valence n; and

RN is a $C_1$–$C_{20}$ organic compound having at least one amine > functional group of $pK_a \not< 7$.

It is recognized that, particularly when the composition contains tetrahedral framework aluminum, a fraction of the amine functional groups may be protonated. The doubly protonated form, in conventional notation, would be $(RNH)_2O$ and is equivalent in stoichiometry to $2 RN + H_2O$.

The characteristic X-ray diffraction pattern of the synthetic zeolite ZSM-48 has the following significant lines:

| Characteristic Lines of ZSM-48 | |
|---|---|
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in angstroms, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | | BROAD | PREFERRED |
|---|---|---|---|
| $Al_2O_3/SiO_2$ | = | 0 to 0.02 | 0 to 0.01 |
| $Na/SiO_2$ | = | 0 to 2 | 0.1 to 1.0 |
| $RN/SiO_2$ | = | 0.01 to 2.0 | 0.05 to 1.0 |
| $OH^-/SiO_2$ | = | 0 to 0.25 | 0 to 0.1 |
| $H_2O/SiO_2$ | = | 10 to 100 | 20 to 70 |
| $H^+$ (added) $SiO_2$ | = | 0 to 0.2 | 0 to 0.05 | wherein RN is a $C_1$–$C_{20}$ organic compound having amine functional group of $pK_a \geq 7$. The mixture is maintained at 80°–250° C. until crystals of the material are formed. $H^+$(added) is moles acid added in excess of the moles of hydroxide added. In calculating $H^+$(added) and OH values, the term acid ($H^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of $pk_a \geq 7$, as defined above, and includes such compounds as $C_3$–$C_{18}$ primary, secondary, and tertiary amines, cyclic amine (such as piperidine, pyrrolidine and piperazine), and polyamines such as $NH_2$—$C_nH_{2n}$—$NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

ZSM-48 is more particularly described in the pending U.S. application filed Nov. 18, 1980 (serial number unknown at this date) which is a continuation of application Ser. No. 064,703, filed Aug. 8, 1979, the entire contents of which are incorporated herein by reference.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occuring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The process of this invention is conducted so that a gaseous parffinic feed containing a high percentage of ethane is contacted with the ZSM-5 type crystalline aluminosilicate zeolite catalyst in a reaction zone, such as, for example, a fixed bed of catalyst composition under effective conversion conditions. In a typical embodiment of the process of this invention, the stream of high ethane content is introduced into the reaction zone at a temperature within the range of 482.2° C. (900° F.) and about 760° C. (1400 F.), a pressure within the range of $1 \times 10^5$ pascal (atmospheric pressure) to $28.6 \times 10^5$ pascal (400 psig) and a WHSV of 0.1 to 5.

Preferred temperature for the process of this invention fall within the range of about 593.3° C. (1100° F.) to about 676.7° C. (1250° F.) and preferred pressures fall within the range of $1 \times 10^5$ pascal (one atmosphere) to $7.9 \times 10^5$ pascal (100 psig). A preferred WHSV is between 0.2 and 2.

The effluent from the reaction zone is separated and distilled to remove the desired aromatic product and the remainder is recycled for further reaction.

EXAMPLE

A quantity of acid or hydrogen-form ZSM-5 zeolite catalyst having a silica to alumina mole ratio of 40 and comprising 65% zeolite and 35% alumina as binder was impregnated with gallium in concentration of 1 and 0.5 percent by weight of gallium in the dried catalyst (zeolite plus alumina). Ethane was flowed through samples of the catalyst impregnated at each concentration. For comparison purposes, a prior art catalyst which was a ZSM-5 zeolite impregnated with 1 percent zinc and 0.25% copper was also treated. Test results for all three types of catalysts are shown in the following table.

TABLE 1

| Run Number | 1 | 2 | 3 | 4 | 5 | 6 |
|---|---|---|---|---|---|---|
| Concentration of Metal in Catalyst (Zeolite + binder)** | 1% Ga | | 0.5% Ga | | 1% Zn/0.25% Cu | |
| Conditions: | | | | | | |
| Temp, °C. | 565.6 | 587.8 | 565.6 | 621.1 | 621.1 | 621.1 |
| Temp, °F. | 1050 | 1090 | 1050 | 1150 | 1100 | 1100 |
| Pressure, pascal | 14.5 | 14.5 | 14.5 | 14.5 | 14.5 | 14.5 |
| Pressure, psig | 0 | 0 | 0 | 0 | 0 | 0 |
| WHSV | 0.5 | 0.5 | 0.5 | 0.5 | 0.43 | 0.65 |
| Time on stream, Hrs | 0.3 | 2.0 | 0.5 | 3.0 | 0.2 | 0.67 |
| Wt. % of ethane converted | 15 | 21 | 11 | 33 | 32 | 35 |
| Selectivity, grams of aromatics produced per 100 grams of ethane converted | 59 | 56 | 64 | 58 | 35 | 32 |
| Product analysis wt. % | | | | | | |
| $C_1$ | 4.4 | 7.5 | 3.0 | 11.3 | 11.6 | 12.1 |
| $C_2=$ | 1.1 | 1.6 | 0.6 | 1.4 | 1.0 | 0.9 |
| $C_2°$ | 84.7 | 78.7 | 88.7 | 66.9 | 67.5 | 65.4 |
| $C_3=$ | — | — | 0.1 | 0.1 | — | — |
| $C_3$ | — | — | 0.2 | 0.3 | — | — |
| $C_4=$ | 0.2 | 0.2 | — | — | — | — |
| $C_4$ | 0.6 | — | — | — | 0.9 | — |
| $C_5 + C_6$ | — | — | — | — | — | — |
| Bz | 5.0 | 7.4 | 4.1 | 12.6 | 5.7 | 6.3 |
| Toluene | 2.7 | 3.6 | 2.6 | 5.6 | 3.9 | 4.2 |
| EB | 0.1 | 0.1 | — | 0.1 | | |
| p-xylene | 0.7* | 0.5* | 0.5* | 0.1 | 0.8* | 0.7* |
| m-xylene | | | | 0.6 | | |
| o-xylene | 0.3 | 0.2 | — | 0.2 | | |
| $C_9+$ | 0 | 0 | — | 0.1 | 8.6 | 10.4 |
| Total | 99.8 | 99.8 | 100.0 | 99.3 | 100.0 | 100.0 |
| Yield, grams of aromatics/100 grams ethane charged | 8.8 | 11.8 | 7.2 | 19.3 | 10.4 | 11.2 |

*para- and meta-xylene combined.
**Catalyst in each run was preconditioned by first being heated at 537.8° C. (1000° F.) in a helium atmosphere and subsequently at 537.8° C. (1000° F.) in a hydrogen atmosphere.

The runs with the zinc-copper catalyst resulted in more $C_9+$ product than those runs with the gallium-impregnated catalyst. Selectivity to the formation of benzene, toluene and xylenes was better when the gallium-impregnated catalysts were used. At a conversion rate of 33 percent, runs with the gallium catalyst resulted in the production of 50 percent more benzene, toluene and xylenes.

What is claimed is:

1. A process for producing aromatic compounds which comprises contacting under conversion conditions, a gaseous paraffinic hydrocarbon feed containing ethane, with a catalyst comprising gallium and a crystalline zeolite characterized by a constraint index within the approximate range of 1 to 12 and a silica to alumina ratio of at least 12, the weight of gallium in said catalyst being between about 0.05 to about 10 percent based on the total weight of catalyst whereby ethane present in said gaseous feed is converted to aromatic compounds, and recovering said aromatic compounds as liquids.

2. The process of claim 1 wherein the conversion conditions include a temperature of from about 480° C. to about 760° C., a pressure of from about $1 \times 10^5$ to about 30 pascal and a WHSV of from about 0.1 to about 5.

3. The process of claim 1 wherein said crystalline zeolite is selected from the group consisting of ZSM-5, ZSM-11, ZSM-12, ZSM-35, and ZSM-38.

4. The process of claim 3 wherein said zeolite is an acid form.

5. The process of claim 4 wherein said zeolite is a HZSM-5 zeolite.

6. The process of claim 1 wherein said zeolite is ZSM-5.

7. The process of claim 1 wherein said zeolite is ZMS-11.

8. The process of claim 1 wherein said zeolite is ZSM-12.

9. The process of claim 1 wherein said zeolite is ZSM-35.

10. The process of claim 1 wherein said zeolite is ZSM-38.

11. The process of claim 1 wherein the concentration of gallium in said catalyst is between about 0.5 and about 5 percent by weight.

12. The process of claim 1 wherein said catalyst composition is composited with a porous matrix material in a proportion of between about 1 to about 99 percent by weight of catalyst composition in the dry composite.

13. The process of claim 1 wherein said catalyst composition is composited with a porous matrix material in a proportion of between about 5 to about 80 percent by weight of catalyst composition in the dry composite.

14. The process of claim 1 wherein the conversion conditions include a temperature of from about 590° C. to about 680° C., a pressure from about $1 \times 10^5$ to about $8 \times 10^5$ pascal and a WHSV of from about 0.2 to about 2.

15. The process of claim 1 wherein the weight of gallium in said catalyst is between about 0.5 and about 5 percent, said zeolite is ZSM-5, said catalyst is composited with a porous matrix material in a proportion of between about 5 and about 80 percent by weight of catalyst composition in the dry composite, and conversion conditions include a temperature of from about 590° C. to about 680° C., a pressure of from about $1 \times 10^5$ to about $8 \times 10^5$ pascal and a WHSV of about 0.2 to about 2.

* * * * *